US008932645B2

(12) United States Patent
Comanor

(10) Patent No.: US 8,932,645 B2
(45) Date of Patent: *Jan. 13, 2015

(54) COMPOSITION AND METHODS FOR RELIEF OF CHEMICAL SENSITIVITY

(71) Applicant: Jeffrey Comanor, Kennesaw, GA (US)

(72) Inventor: Jeffrey Comanor, Kennesaw, GA (US)

(73) Assignee: Coastal Biologic Solutions, Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/320,958

(22) Filed: Jul. 1, 2014

(65) Prior Publication Data
US 2014/0314730 A1    Oct. 23, 2014

Related U.S. Application Data

(63) Continuation-in-part of application No. 13/060,517, filed as application No. PCT/US2009/055281 on Aug. 28, 2009, now Pat. No. 8,815,300.

(60) Provisional application No. 61/092,892, filed on Aug. 29, 2008.

(51) Int. Cl.
*A61K 31/40* (2006.01)
*A61K 31/28* (2006.01)
*A61K 31/122* (2006.01)
*A61K 33/42* (2006.01)
*A61K 31/201* (2006.01)
*A61K 31/519* (2006.01)

(52) U.S. Cl.
CPC .............. *A61K 31/28* (2013.01); *A61K 31/122* (2013.01); *A61K 33/42* (2013.01); *A61K 31/201* (2013.01); *A61K 31/519* (2013.01)
USPC ........... 424/605; 424/601; 424/646; 424/617; 514/690

(58) Field of Classification Search
None
See application file for complete search history.

(56) References Cited

U.S. PATENT DOCUMENTS

| 6,352,712 B1* | 3/2002 | Lukaczer et al. .............. 424/439 |
| 2005/0227961 A1 | 10/2005 | Kucharik et al. |
| 2006/0094685 A1 | 5/2006 | Endo et al. |

FOREIGN PATENT DOCUMENTS

EP            1323422         7/2003

OTHER PUBLICATIONS

"Health encyclopedia: Molybdenum". Swanson Health Products. http://web.archive.org/web/20120421161319/http://www.swansonvitamins.com/health-library/encyclopedia/minerals/molybdenum.html, cached Apr. 21, 2012.*

Dr. Hoffman's NT Factor Energy, http://www.drhoffman.com/downloads/ntfactorenergy.pdf, Wayback Machine dates to Oct. 2007.
Dr. Murphree's, http://www.drmurphreestore.com/healthnews504.html, dated Sep. 2007.
ABC Homeopathy, http://abchomeopathy.com/rphp/Ph-ac, accessed Oct. 3, 2013, wayback machine archived page dated Oct. 8, 2003.
HolisticOnline; http://www.holistic-online.com/remedies/cfs/cfs_homeopathy.htm, Feb. 19, 2001.
Dr. Teitelbaum's treatment protocol; http://www.immunesupport.com/chronic-fatigue-syndrome-teitelbaum.htm, Nov. 27, 2006.
Stedman's Online. 2012.
Sahley BJ. Alpha KG—fatigue fighter. Pain & Stress Publications. 2006.
Nihalani et al. Fibromyalgia—a review for the psychiatrist. Psychiatry. 2006;44-60.
Magnesium. IBISmedical. 2000.
FMS Information Resource Guide. Will vitamins and supplements help treat fibromyalgia syndrome? Immune Support. 2000.
Chemical characteristics. The Olive Oil Source. 2012.
Byrnes S. Solving the puzzle of fibromyalgia. 2004. 1-6.
Stavarache et al. Fatty acids methyl esters from vegetable oil by means of ultrasonic energy. Ultrasonics Sonochemistry. 2005;12:367-372.
Santos et al. Thermoanalytical, kinetic and theological parameters of commercial edible vegetable oils. Journal of Thermal Analysis and Calorimetry. 2004;75:419-428.
Choline. WebMD. 2009.
J. Das-Munshi, G. J. Rubin, S. Wessely, Multiple chemical sensitivities: A systematic review of provocation studies, Journal of Allergy and Clinical Immunology, 118, pp. 1257-1264 (2006).
Gibson, P. R.; Elms, A. N.; Ruding, L. A. (2003). "Perceived treatment efficacy for conventional and alternative therapies reported by persons with multiple chemical sensitivity". Environmental health perspectives 111 (12): 1498-1504.
Magill MK, Suruda A (Sep. 1998). "Multiple chemical sensitivity syndrome". Am Fam Physician 58 (3): 721-8.
Graveling RA, Pilkington A, George JPK, Butler MP, Tannahill SN (1999). "A review of multiple chemical sensitivity". Occupational and Environmental Medicine 56 (2): 73-85.

(Continued)

*Primary Examiner* — Mina Haghighatian
*Assistant Examiner* — Erin Hirt
(74) *Attorney, Agent, or Firm* — Thomas|Horstemeyer, LLP

(57) ABSTRACT

The formulations of the present disclosure alter the perception of symptoms, especially as experienced by subjects reporting the characteristic features associated with the syndrome known as multiple chemical sensitivity (MCS). The present disclosure encompasses formulations for the relief of symptoms associated with MCS, where the formulations comprise orthophosphoric acid, a vegetable oil comprising an esterified mono-unsaturated fatty acid, folic acid, and a molybdenum salt. The formulations can further comprise magnesium citrate, magnesium aspartate, malic acid, L-carnitine, alpha-ketoglutaric acid, co-enzyme Q10, glycerol, inositol, and choline bitartrate, optionally Q10, and riboflavin to provide a yellow color to the formulation. Another aspect of the disclosure are methods for alleviating MCS-related symptoms in subject human, comprising: providing to a subject an effective dose of a formulation comprising orthophosphoric acid, a mono-unsaturated fat, folic acid, molybdenum, and water.

5 Claims, No Drawings

(56) References Cited

OTHER PUBLICATIONS

Binkley KE, Kutcher S. Panic response to sodium lactate infusion in patients with multiple chemical sensitivity syndrome. J Allergy Clin Immunol 1997;99:570-4.

E. Shorter, Multiple chemical sensitivity: pseudodisease in historical perspective, Scand J Work Environ Health 23 (1997) (suppl 3), pp. 35-42.

Pall ML (Sep. 2003). "Elevated nitric oxide/peroxynitrite theory of multiple chemical sensitivity: central role of N-methyl-D-aspartate receptors in the sensitivity mechanism". Environ. Health Perspect. 111 (12): 1461-4.

Reid, S et al. (2001) Multiple Chemical Sensitivity and Chronic Fatigue Syndrome in British Gulf War Veterans. American Journal of Epidemiology vol. 153, No. 6, pp. 604-609.

Nawab SS et al. Self-reported sensitivity to chemical exposures in five clinical populations and healthy controls. Psychiatry Res. Jul. 24, 2000;95(1):67-74.

Pall ML (Sep. 2002). "NMDA sensitization and stimulation by peroxynitrite, nitric oxide, and organic solvents as the mechanism of chemical sensitivity in multiple chemical sensitivity". FASEB J. 16 (11): 1407-17.

* cited by examiner

COMPOSITION AND METHODS FOR RELIEF OF CHEMICAL SENSITIVITY

CROSS-REFERENCE TO RELATED APPLICATION

This application is a continuation-in-part of U.S. patent application Ser. No. 13/060,517, filed on May 3, 2011, which claims priority to PCT Application No. US/2009/055281, filed Aug. 28, 2009 and entitled "COMPOSITION AND METHODS FOR RELIEF OF NEUROPATHOLOGICAL PAIN", and which claims priority to U.S. Provisional Application No. 61/092,892, entitled "COMPOSITION AND METHODS FOR RELIEF OF NEUROPATHOLOGICAL PAIN" filed on Aug. 29, 2008, the entireties of which are herein incorporated by reference in its entirety.

TECHNICAL FIELD

The present disclosure is generally related to a composition and methods for the relief of symptoms associated with chemical sensitivity. The present disclosure is especially related to compositions and methods for the relief of symptoms associated with chemical sensitivity.

BACKGROUND

Fibromyalgia is a chronic disorder characterized by widespread musculoskeletal pain and tenderness to palpation at specific tender points. In addition, fibromyalgia patients often describe other symptoms such as fatigue, sleep disturbances, headache or cognitive dysfunction associated with the syndrome. The American College of Rheumatology has defined fibromyalgia as pain in all four quadrants combined with axial skeletal pain, and at least 11 of 18 tender point sites. Widespread pain must have been present for at least 3 months. Tender points, the diagnostic hallmark of fibromyalgia, are examples of hyperalgesia, thought to be due to central sensitization. Patients with fibromyalgia have quantitatively altered perception compared to pain-free patients, suggesting that people with fibromyalgia process sensory information differently, most likely due to changes in the central processing of pain at the spinal level.

Patients often report widespread pain over all parts of the body which often seems to arise in the muscles. The pain shows varying intensities that wax and wane over time, it is profound, widespread and chronic, and is often severely debilitating, having profound effects on the quality of life of the patients.

Typically, the pain is described as deep muscular aching, throbbing, twitching, stabbing and shooting pain. Neurological complaints such as numbness, tingling and burning are often present. The severity of the pain and stiffness is often worse in the morning. Aggravating factors that affect pain include cold/humid weather, non-restorative sleep, physical and mental fatigue, excessive physical activity, physical inactivity, anxiety and stress. Additionally to pain, patients commonly complain of fatigue in form of an all-encompassing exhaustion that interferes with even the simplest daily activities. Within the spectrum of symptoms are a decreased sense of energy, disturbances of sleep, problems with memory and concentration and varying degrees of anxiety and depression.

Certain other medical conditions are sometimes associated with fibromyalgia, such as tension headaches, migraine, irritable bowel syndrome, overactive bladder, pelvic pain, premenstrual tension syndrome, cold intolerance, dry eyes and mouth, anxiety, depression, ringing in the ears, dizziness, vision problems and others. Patients with established rheumatoid arthritis, lupus (SLE) and Sjogren's syndrome often develop fibromyalgia symptoms during the course of their disease.

The complexity of the syndrome, with multiple and highly diverse symptoms described by the patients has meant that effective and long-term relief, above all of the pain, has proved elusive. Common analgesics have limited effectiveness, especially over the long-term.

Multiple chemical sensitivity (MCS) is a chronic medical condition characterized by symptoms that the affected person attributes to low-level chemical exposure. Commonly accused substances include, but are not limited to, scented products, petroleum products, and paint fumes. Symptoms are often subjective and non-specific, such as nausea, fatigue, dizziness and headaches, but also be manifested by more objective symptoms such as inflammation of skin, joints, gastrointestinal tract and airways. While MCS has not been recognized as an organic, chemical-caused syndrome, many in the healthcare profession believe MCS symptoms or attributed to psychological issues, many people with severe symptoms are disabled as a result.

Official recognition, while limited in the U.S., has advanced in a number of other countries such as Australia and with the recognition that affected people are clinically sick. Although they recognize the existence of the syndrome, however, there is no agreement on the actual causation. Furthermore, the U.S. Social Security issued a court memorandum officially recognizing MCS "as a medically determinable impairment" on an agency-wide basis. That is, without making any statement about the cause of MCS or the role of chemicals in MCS, the Social Security administration agrees that some MCS patients are too disabled to be meaningfully employed.

SUMMARY

The formulations of the present disclosure alter the perception of sensitivity after exposure to low doses of chemicals, especially as experienced by subjects reporting the characteristic features associated with the syndrome known as multiple chemical sensitivity (MCS). The formulations of the present disclosure further provide relief from multiple symptoms associated with MCS. It has been found that the inclusion of molybdenum is significant to providing the relief from the symptoms of MCS.

Accordingly, the disclosure encompasses embodiments of a formulation for reducing chemical sensitivity of a recipient subject, and methods of its use, the formulation consisting of orthophosphoric acid, a vegetable oil comprising an esterified mono-unsaturated fatty acid, folic acid, magnesium citrate, magnesium aspartate, malic acid, L-carnitine, alpha-ketoglutaric acid, co-enzyme Q10, glycerol, inositol, choline bitartrate, molybdenum glycinate, water, and optionally riboflavin.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

DEFINITIONS

In describing and claiming the disclosed subject matter, the following terminology will be used in accordance with the definitions set forth below.

The term "formulation" as used herein refers to a composition that may be a stock solution of the components, or a composition, preferably including a dilutant such as water or other pharmaceutically acceptable carrier, that may be available for distribution including to a patient or physician.

The term "vegetable oil" as used herein refers to oils comprising a triglyceride ester of a mono-unsaturated long-chain fatty. Vegetable oils for use in the formulations of the disclosure include, but are not limited to, coconut oil, corn oil, cottonseed oil, olive oil, palm oil, peanut oil rapeseed oil, safflower oil, sesame oil, soybean oil, and sunflower oil. For example, but not intending to be limiting, olive oil is composed mainly of the mixed triglyceride esters of oleic acid and palmitic acid and of other fatty acids, along with traces of squalene (up to 0.7%) and sterols (about 0.2% phytosterol and tocosterols). The composition varies by cultivar, region, altitude, time of harvest, and extraction process. Olive oil further comprises natural products with potent antioxidant properties which give extra-virgin unprocessed olive oil its bitter and pungent taste and which are esters of tyrosol, hydroxytyrosol, oleocanthal and oleuropein.

The term "mono-unsaturated fat" as used herein refers to fatty acids that have a single double bond in the fatty acid chain and all of the remainder of the carbon atoms in the chain are single-bonded. By contrast, polyunsaturated fatty acids have more than one double bond.

Fatty acids are long-chained molecules having a methyl group at one end and a carboxylic acid group at the other end. Fatty acid fluidity increases with increasing number of double bonds. Therefore, mono-unsaturated fatty acids have a higher melting temperature than polyunsaturated fatty acids but lower than saturated fatty acids. Mono-unsaturated fatty acids are liquids at room temperature and semisolid or solid when refrigerated. Common mono-unsaturated fatty acids are palmitoleic acid, cis-vaccenic acid, and oleic acid. Palmitoleic acid has 16 carbon atoms with the first double bond occurring 7 carbon atoms away from the methyl group (and 9 carbons from the carboxyl end). It can be lengthened to the 18-carbon cis-vaccenic acid. Oleic acid has 18 carbon atoms with the first double bond occurring 9 carbon atoms away from the methyl group.

The term "coloring agent" as used herein refers to any agent pharmaceutically acceptable or otherwise certified as same for human ingestion, such as, but not limited to, riboflavin, and which may impart to the formulations of the disclosure either an attractive appearance or to distinguish the formulation from a colorless liquid such as water, or to provide a means to determine the dilution of a formulation.

The term "flavoring agent" as used herein refers to any agent pharmaceutically acceptable or otherwise certified as same for human ingestion that imparts to a formulation of the disclosure a flavor that may increase the palatability of the composition to a patient receiving the formulation.

The term "neuropathy" as used herein refers to any diseases of the nervous system. Peripheral neuropathy refers to pain associated with muscle weakness, impaired reflexes and the like such as, but not limited to, polyneuropathy.

The term "fibromyalgia" as used herein refers to chronic and frequently difficult-to-manage pain in muscle and soft tissues surrounding the joints. Associated with pain are other symptoms that may not be present in the entirety such as depression, memory loss, anxiety and sleeplessness.

The term "Multiple Chemical Sensitivity (MCS)" as used herein refers to symptoms that may be mild to disabling. Six consensus criteria have been identified by researchers for the diagnosis and definition of MCS including: symptoms reproducible with repeated chemical exposures; the condition has persisted for a significant period of time; low levels of exposure result in manifestations of the syndrome; symptoms improve or resolve completely when the triggering chemicals are removed; responses often occur to multiple chemically unrelated substances; and symptoms involve multiple-organ symptoms. Symptoms may be physical or psychological in nature and are essentially those that are disruptive to the individuals' mental or physical wellness and that the individual attributes to exposure to a chemical or scent. Common symptoms are vague, non-specific complaints: feeling tired, "brain fog" (short-term memory problems, difficulty concentrating) and muscle pain. These complaints are common to a large number of medical conditions from psychiatric conditions, such as major depressive disorder, to neurological conditions, such as orthostatic intolerance, to sleep disorders, high blood pressure, autoimmune diseases, cancer, difficulty breathing, pains in the throat, chest, or abdominal region, asthma, skin irritation, contact dermatitis, and hives or other forms of skin rash, headaches, neurological symptoms (nerve pain, pins and needles feelings, weakness, trembling, restless leg syndrome, etc.), tendonitis, seizures, visual disturbances (blurring, halo effect, inability to focus), extreme anxiety, panic and/or anger, sleep disturbance, suppression of immune system, digestive difficulties, nausea, indigestion/heartburn, vomiting, diarrhea, joint pains, vertigo/dizziness, abnormally acute sense of smell (hyperosmia), sensitivity to natural plant fragrance or natural pine terpenes, insomnia, dry mouth, dry eyes, and an overactive bladder. Environmental medicine specialists claim MCS causes negative health effects in multiple organ systems, and respiratory distress, seizures, cognitive dysfunction, heart arrhythmia, nausea, headache, and fatigue can result from exposure to levels of common chemicals that are normally deemed as safe.

There have been clinical trials that both support and don't support the claim that the symptoms of multiple chemical sensitivity (MCS) are caused by chemicals. Multiple chemicals have been reported to trigger MCS symptoms. In addition to anything that is perfumed or scented, exposure to commonly encountered chemicals found in food (including but not limited to tartrazine, caffeine, monosodium glutamate, not allergic food intolerances, cleaning agents, pesticides, perfumes, vehicle exhaust, hair-dressing products, new carpeting, new furniture, chlorine in water, fresh ink, wood smoke, secondhand tobacco smoke, gasoline or diesel fuel, petroleum jelly, tar, or asphalt, agricultural chemicals, dry cleaning fluid, formaldehyde; glues, varnishes, polishes, paints, solvents, paint thinners, and volatile organic compounds (VOCs), bleach, fabric softeners, wool-wash, and laundry detergents, lotion, aftershave lotion, nail polish, or skin care products such as soaps, air fresheners, deodorizers and scented candles, dishwashing liquid and dishwasher detergent, and marking pens) can trigger reactions in the respondents.

While it has been suggested that there is a placebo effect in the perception of sensitivity to low levels of chemicals, it has also be concluded, for example, that genotyped patients diagnosed with MCS, with suspected MCS, and healthy controls, suggest inhibition of expression and activity of metabolizing and antioxidant enzymes in MCS, accelerated lipid oxidation, increased nitric oxide production and glutathione depletion and increased plasma inflammatory cytokines. Accordingly, while the suffers have a clear perception of disabling symptoms, the causes remain undefined.

Some possible explanations for diagnosing MCS include manifestations of migraine, anxiety disorder, lupus, postural orthostatic tachycardia syndrome or other forms of orthostatic intolerance, hay fever and other allergies, hypercalcemia, hypothyroidism, chronic fatigue syndrome, fibromyalgia, or mast cell activation diseases such as mastocytosis, where symptoms such as brain fog and headaches can be triggered by chemicals or inhalants. Some sufferers may also have a tendency to misinterpret benign physical symptoms or simply have a disturbingly acute sense of smell. While psychological causes have also not been definitively excluded, studies have suggested neurological triggers, genetic differences in metabolism, immune dysregulation, and emotional stresses.

DESCRIPTION

The embodiments of the present disclosure encompass novel formulations and methods of use thereof intended for the effective relief of symptoms typically associated with the syndrome known as multiple chemical sensitivity. The formulations and methods of the disclosure are further intended to provide relief to symptoms other than just pain that may be associated with multiple chemical sensitivity, including but not limited to, depression, memory loss, anxiety and sleeplessness. The formulations of the disclosure may also be beneficial in the relief of pain or ancillary symptoms associated with inflammatory diseases, including, but not limited to, rheumatoid arthritis, lupus, polyneuropathic disease and the like. It has been shown, that the combination of orthophosphoric acid, a mono-unsaturated fatty acid (in particular the naturally derived preparation of such fatty acids in olive oil), folic acid, and molybdenum glycinate provide rapid relief from the perceived symptoms associated with multiple chemical sensitivity (MCS). Pain relief and alleviation of mood-altering conditions such as depression, anxiety and the like have also been reported when the formulations of the disclosure are administered to subjects apparently experiencing inflammatory syndromes including lupus, rheumatoid arthritis and chronic allergies.

The formulations of the disclosure have been administered to a group of patients, both male and female and of ages ranging from about 19 to about 75 years. Controlled studies, where some patients were administered placebo control formulations such as water dispensed to the patients in a manner identical to that of the actual formulations, showed that the placebos had no reported effect in alleviating the symptoms of MCS. Additionally, no adverse side effects were reported. Many patients also reported that with the formulations of the disclosure, not only was there immediate or rapid relief of the pain symptoms that had afflicted many for years, but other symptoms associated with MCS were lessened or relieved. Many of the treated subjects experience long-lasting, if not permanent, relief from MCS and if the symptoms returned, further administration of the formulations of the disclosure provide rapid and prolonged relief of undesired symptoms associated with MCS.

The formulation of the present disclosure appears, therefore, to alter the perception of reaction to exposure to low levels of environmental chemicals, especially as experienced by subjects reporting the characteristic features associated with the syndrome known as MCS. In particular, while the formulation lacking the molybdenum glycinate is effective for alleviating the symptoms of fibromyalgia, it has been unexpectedly found that the presence of molybdenum glycinate in the formulations of the disclosure is effective to provide a reduction in the perceived MCS symptoms of the subject. The present disclosure, therefore, provides formulations ranging from an undiluted composition to diluted formulations, both of which may be suitable to administer to a patient, including by, but not limited to, undiluted dose deposition directly to oral tissue, or in a more diluted fashion intended to be ingested orally by the patient.

The administered dose is dependent on the severity of the perceived symptoms of the subject. An initial dose of between about 9 ml and about 12 ml of the stock solution, as shown in Example 4, is diluted in between about 1.5 fluid ounces and 3.0 fluid ounces of water. The subject receives the full diluted dose and is retested for symptoms of MCS within about 30 secs. If there is no evident relief of pain experienced, a second dose of the formulation may be given. The second dose is between about 6 ml and about 9 ml of the stock solution diluted by the same amount of water as before, and again fully ingested by the subject. The full effects of symptom relief may be seen within 15 minutes of administering the first dose.

Most advantageously, it has been found that a patient can receive from about 2 to about 7 drops, or even more drops to about 10 or 12 drops depending upon the patient and the severity of the manifestation of MCS. Such doses can be delivered advantageously twice per day, i.e. once in the morning and once later. For children, a dose of about 3 to about 4 drops administered twice daily has been found to be useful. Since the advantageous effects of a dose may be prolonged, it has been found that a recurrence of MCS is possible. Thus it is contemplated that repeat doses of the formulations of the disclosure may be required to prophylactically anticipate and counteract the onset of MCS-related symptoms.

In one extended study of the efficacy of the formulations of the disclosure on relieving subjects of perceived symptoms associated with MCS, of about 34 subjects receiving the formulation according to the methods of the disclosure, only 2 reported no relief. In this study cohort, the subjects were aged from 18-66, mostly Caucasian females. In the early stage of the treatment, most subjects appear to require about 3 ml to about 4 ml of the formulation presented in Example 4. The exact amount administered to the patient depends, however, on the severity of the symptoms—the greater the discomfort; the more of the formulation was administered. After about 1 to 2 weeks of treatment, the dose can typically be reduced to about 3 mls of the formulation diluted in water, and taken by the subject every 7 to 8 hours. If the symptom relief is sufficiently controlled after more than a month, the dosage may be reduced even further to between about 0.5 to about 3 mls every 8 to 10 hours. Subjects could, after about 6 months of taking the formulation cease further treatment for several weeks or months, although there were some subjects who reverted to their MCS and required subsequent doses of the formulation of the disclosure. In many cases, full and apparently permanent relief of MCS has been described by the subjects. None of the subjects reported sensitivity to the components of the administered formulation, and most reported that they could subsequently tolerate being in the vicinity of such as perfumes that had previously resulted in severe adverse reactions.

As an alternative to the ingestion of the diluted formulation by the subject, the undiluted formulation may be administered sublingually, i.e. under the tongue. It has been observed that this method provides relief symptoms of MCS within a few seconds or minutes.

One aspect of the disclosure encompasses embodiments of a formulation for reducing chemical sensitivity of a recipient subject, the formulation consisting of orthophosphoric acid, a vegetable oil comprising an esterified mono-unsaturated fatty acid, folic acid, magnesium citrate, magnesium aspartate, malic acid, L-carnitine, alpha-ketoglutaric acid, co-enzyme Q10, glycerol, inositol, choline bitartrate, molybdenum glycinate, water, and optionally riboflavin.

In one embodiment of this aspect of the disclosure, the formulation of claim 1 consists of, in a final volume of 100 ml: orthophosphoric acid between about 4 ml to about 16 ml; vegetable oil between about 0.25 ml to about 10 ml; folic acid between about 0.1 mg and about 10 mg; malic acid between about 1 mg and about 5000 mg; magnesium citrate between about 1 mg and about 5000 mg; magnesium aspartate between about 1 mg and about 100 mg; L-carnitine between about 1 mg and about 1000 mg; alpha-ketoglutaric acid between about 1 mg and about 1000 mg; choline bitartrate between about 1 mg and about 100 mg; inositol between about 1 mg and about 100 mg; glycerol between about 0.1 ml and about 5 ml; Q10 between about 0.05 mg and about 1000 mg, molybdenum glycinate between 50 mg and about 250 mg, and water, and optionally riboflavin.

In another embodiment of this aspect of the disclosure, the formulation consists of, in a final volume of 100 ml: orthophosphoric acid, about 8.5 ml; vegetable oil, about 1.2 ml; folic acid, about 2.1 mg; malic acid, about 85 mg; magnesium citrate, about 170 mg; magnesium aspartate, about 17 mg; L-carnitine, about 85 mg; alpha-ketoglutaric acid, 127 mg; choline bitartrate, about 11 mg; inositol, about 23 mg; glycerol between about 0.1 ml and about 0.5 ml; Q10 between about 0.05 mg and about 1000 mg, molybdenum glycinate, about 109 mg; water; and optionally riboflavin.

Another aspect of the disclosure encompasses embodiments of a method for reducing chemical sensitivity in a subject, the method comprising: providing to a subject in need of relief from chemical sensitivity an effective dose of a formulation consisting of orthophosphoric acid, a vegetable oil comprising an esterified mono-unsaturated fatty acid, folic acid, magnesium citrate, magnesium aspartate, malic acid, L-carnitine, alpha-ketoglutaric acid, co-enzyme Q10, glycerol, inositol, choline bitartrate, molybdenum glycinate, water, and optionally riboflavin.

In one embodiment of this aspect of the disclosure, the formulation consists of, in a final volume of 100 ml: orthophosphoric acid, about 8.5 ml; vegetable oil, about 1.2 ml; folic acid, about 2.1 mg; malic acid, about 85 mg; magnesium citrate, about 170 mg; magnesium aspartate, about 17 mg; L-carnitine, about 85 mg; alpha-ketoglutaric acid, 127 mg; choline bitartrate, about 11 mg; inositol, about 23 mg; glycerol between about 0.1 ml and about 0.5 ml; Q10 between about 0.05 mg and about 1000 mg, molybdenum glycinate, about 109 mg; water; and optionally riboflavin.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

In preparing any of the formulations of this and any of the following examples, the order in which the components are combined may be varied. However a preferred order comprises adding dry components to the orthophosphoric acid followed by vigorous agitation. The mono-unsaturated fatty acid component may then be added with further agitation to forma an emulsion or near-emulsion. The water component may then be added with a final mixing to provide a homogeneous or near homogenous liquid. It is contemplated, however, that the mixing order may tolerate some variation such as adding the dry components to the water before adding to the orthophosphoric acid and the mono-saturated fatty acid.

Example 2

A formulation consisting of orthophosphoric acid, a vegetable oil comprising an esterified mono-unsaturated fatty acid, folic acid, magnesium citrate, magnesium aspartate, malic acid, L-carnitine, alpha-ketoglutaric acid, co-enzyme Q10, glycerol, inositol, choline bitartrate, molybdenum glycinate, water, and optionally riboflavin.

Example 3

A formulation consisting of, in a final volume of 100 ml: orthophosphoric acid between about 4 ml to about 16 ml; vegetable oil between about 0.25 ml to about 10 ml; folic acid between about 0.1 mg and about 10 mg; malic acid between about 1 mg and about 5000 mg; magnesium citrate between about 1 mg and about 5000 mg; magnesium aspartate between about 1 mg and about 100 mg; L-carnitine between about 1 mg and about 1000 mg; alpha-ketoglutaric acid between about 1 mg and about 1000 mg; choline bitartrate between about 1 mg and about 100 mg; inositol between about 1 mg and about 100 mg; glycerol between about 0.1 ml and about 5 ml; Q10 between about 0.05 mg and about 1000 mg, molybdenum glycinate between 50 mg and about 250 mg, and water, and optionally riboflavin.

Example 4

A formulation consisting of, in a final volume of 100 ml: ortho-phosphoric acid, about 8.5 ml; vegetable oil, about 1.2 ml; folic acid, about 2.1 mg; malic acid, about 85 mg; magnesium citrate, about 170 mg; magnesium aspartate, about 17 mg; L-carnitine, about 85 mg; alpha-ketoglutaric acid, 127 mg; choline bitartrate, about 11 mg; inositol, about 23 mg; glycerol between about 0.1 ml and about 0.5 ml; Q10 between about 0.05 mg and about 1000 mg, molybdenum glycinate, about 109 mg; water; and optionally riboflavin.

Example 5

The administered dose is dependent on the severity of the perceived symptoms of the subject. An initial dose of between 9 ml and 12 ml of the stock solution is diluted in between about 1.5 fluid ounces and 3.0 fluid ounces of water. The subject receives the full diluted dose. If there is no evident relief of symptoms experienced, a second dose of the formulation may be given. The second dose is between 6 ml and 9 ml of the stock solution diluted by the same amount of water as before, and again fully ingested by the subject. On rare occasions, if symptoms still show no sign of diminishing, and a third dose may be required. The full effects of symptom relief may be seen within 15 minutes of administering the first dose or over an extended time from one day to about a week.

I claim:

1. A formulation for reducing chemical sensitivity consisting of orthophosphoric acid, a vegetable oil comprising an esterified mono-unsaturated fatty acid, folic acid, magnesium citrate, magnesium aspartate, malic acid, L-carnitine, alpha-ketoglutaric acid, co-enzyme Q10, glycerol, inositol, choline bitartrate, molybdenum glycinate, water, and optionally riboflavin.

2. The formulation of claim 1 consisting of, in a final volume of 100 ml: orthophosphoric acid between about 4 ml to about 16 ml; vegetable oil between about 0.25 ml to about 10 ml; folic acid between about 0.1 mg and about 10 mg; malic acid between about 1 mg and about 5000 mg; magnesium citrate between about 1 mg and about 5000 mg; magnesium aspartate between about 1 mg and about 100 mg; L-carnitine between about 1 mg and about 1000 mg; alpha-ketoglutaric acid between about 1 mg and about 1000 mg; choline bitartrate between about 1 mg and about 100 mg; inositol between about 1 mg and about 100 mg; glycerol between about 0.1 ml and about 5 ml; Q10 between about 0.05 mg and about 1000 mg, molybdenum glycinate between 50 mg and about 250 mg, and water, and optionally riboflavin.

3. A formulation consisting of, in a final volume of 100 ml: ortho-phosphoric acid, about 8.5 ml; vegetable oil, about 1.2 ml; folic acid, about 2.1 mg; malic acid, about 85 mg; magnesium citrate, about 170 mg; magnesium aspartate, about 17 mg; L-carnitine, about 85 mg; alpha-ketoglutaric acid, 127 mg; choline bitartrate, about 11 mg; inositol, about 23 mg; glycerol between about 0.1 ml and about 0.5 ml; Q10 between about 0.05 mg and about 1000 mg, molybdenum glycinate, about 109 mg; water; and optionally riboflavin.

4. A method for reducing chemical sensitivity in a subject, comprising: providing to a subject in need of relief from chemical sensitivity an effective dose of a formulation consisting of orthophosphoric acid, a vegetable oil comprising an esterified mono-unsaturated fatty acid, folic acid, magnesium citrate, magnesium aspartate, malic acid, L-carnitine, alpha-ketoglutaric acid, co-enzyme Q10, glycerol, inositol, choline bitartrate, molybdenum glycinate, water, and optionally riboflavin.

5. The method of claim 4, wherein the formulation consists of, in a final volume of 100 ml: ortho-phosphoric acid, about 8.5 ml; vegetable oil, about 1.2 ml; folic acid, about 2.1 mg; malic acid, about 85 mg; magnesium citrate, about 170 mg; magnesium aspartate, about 17 mg; L-carnitine, about 85 mg; alpha-ketoglutaric acid, 127 mg; choline bitartrate, about 11 mg; inositol, about 23 mg; glycerol between about 0.1 ml and about 0.5 ml; Q10 between about 0.05 mg and about 1000 mg, molybdenum glycinate, about 109 mg; water; and optionally riboflavin.

* * * * *